US009194790B2

(12) United States Patent
Kashima

(10) Patent No.: US 9,194,790 B2
(45) Date of Patent: Nov. 24, 2015

(54) STICK-SLIP DETECTING DEVICE AND DETECTING METHOD

(71) Applicant: AZBIL Corporation, Tokyo (JP)

(72) Inventor: Toru Kashima, Tokyo (JP)

(73) Assignee: AZBIL CORPORATION, Chiyoda-Ku, Tokyo (JP)

( * ) Notice: Subject to any disclaimer, the term of this patent is extended or adjusted under 35 U.S.C. 154(b) by 339 days.

(21) Appl. No.: 13/673,751

(22) Filed: Nov. 9, 2012

(65) Prior Publication Data

US 2013/0124132 A1 May 16, 2013

(30) Foreign Application Priority Data

Nov. 10, 2011 (JP) ................. 2011-246248

(51) Int. Cl.
*G01N 19/00* (2006.01)
*F16K 37/00* (2006.01)

(52) U.S. Cl.
CPC ............ *G01N 19/00* (2013.01); *F16K 37/0075* (2013.01); *F16K 37/0083* (2013.01)

(58) Field of Classification Search
CPC .. F16K 37/0075; F16K 37/0083; G01N 19/00

USPC .......... 702/113, 150, 183; 73/1.79, 11.09, 7, 9
See application file for complete search history.

(56) References Cited

U.S. PATENT DOCUMENTS 5,750,879 A * 5/1998 Ohtsuka et al. ..................... 73/9
7,478,012 B2 * 1/2009 Tewes et al. ................... 702/183

FOREIGN PATENT DOCUMENTS

| JP | 10-047313 | 2/1998 |
| JP | 3254624 | 2/2002 |
| JP | 2011-080787 | 4/2011 |

* cited by examiner

*Primary Examiner* — Alexander Satanovsky
(74) *Attorney, Agent, or Firm* — Troutman Sanders LLP

(57) ABSTRACT

A first state quantity and a second state quantity of a valve stem dislocation are calculated, and a ratio of the first state quantity and the second state quantity is calculated as a first stick-slip indicator SSpv in a first stick-slip indicator calculating portion. A third state quantity and a fourth state quantity of a control instruction value of a valve stem dislocation are calculated, and a ratio of the third state quantity and the fourth state quantity is calculated as a second stick-slip indicator SSsp in a second stick-slip indicator calculating portion. With a threshold value as Th, a first constant as $\alpha$, and a second constant as $\beta$, a fault evaluating portion concludes that a stick-slip has occurred when the conditional expression "SSpv>Th AND SSpv>$\alpha$·SSsp+$\beta$" is satisfied.

6 Claims, 12 Drawing Sheets

FIG.12
(a)
Example Wherein Stick-Slip False Detection Is Prevented
SSpv=16.00, SSsp=16.97, Th=10
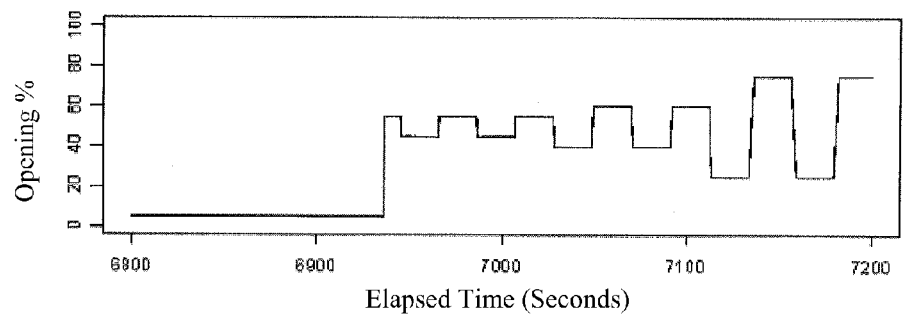
(b)
Example Wherein Stick-Slip False Detection Is Not Prevented
SSpv=10.32, SSsp=10.26, Th=10
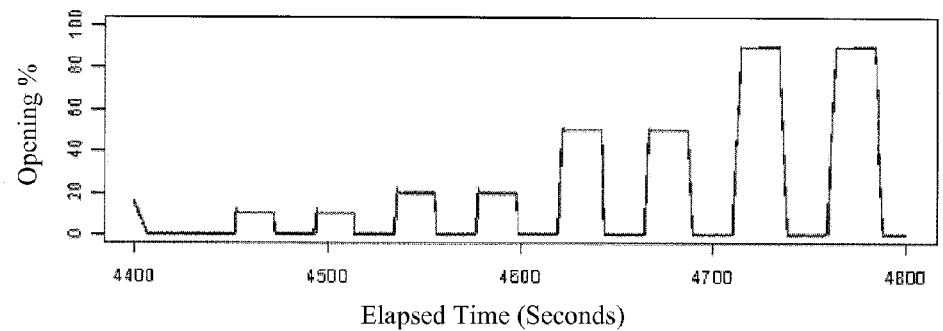

STICK-SLIP DETECTING DEVICE AND DETECTING METHOD

CROSS-REFERENCE TO RELATED APPLICATION

The present application claims priority to Japanese Patent Application No. 2011-246248 filed Nov. 10, 2011. The content of this application is incorporated by reference herein in its entirety.

FIELD OF TECHNOLOGY

The present invention relates to a stick-slip detecting device and detecting method for detecting stick-slip in the operation of a device having a contact sliding portion, such as a regulator valve or a gas governor.

BACKGROUND

Failures in regulator valves or gas governors can be diagnosed by detecting the occurrence of stick-slip in a contact sliding portion. Stick-slip occurs due to the state of a piston 101, a cylinder 102, and a contact sliding portion 103, as illustrated in, for example, FIG. 8. For example, this stick-slip occurs when, for example, contamination incurs into the contact sliding portion 103. Consequently, stick-slip can be detected by detecting the state of a measured dislocation by detecting the dislocation of the piston 101. (See Japanese Patent 3254624 ("JP '624").)

Here a simple explanation will be given regarding the detection of stick-slip set forth in JP '624. In this detecting technique, the dislocation of the piston 101 is detected, a first state quantity is calculated from the detected dislocation, a second state quantity is calculated from the detected dislocation, and a ratio of the first state quantity and the second state quantity obtained from the dislocation during proper operation is compared to a ratio of the calculated first state quantity and second state quantity, to detect (evaluate) the stick-slip. In this detection of stick-slip, the ratio of the first state quantity and the second state quantity may be termed a "stick-slip indicator."

For example, the average of the absolute values of first-order difference values for the dislocation may be used as the first state quantity, and the root mean square of the first-order difference values of the dislocation may be used as the second state quantity. When the dislocations of the piston 101 are detected discreetly and the ith detected dislocation is defined as Xi, then the respective state quantities can be expressed using Expression (1) and Expression (2), below (wherein N is the number of dislocation data used for calculating the state quantities):

[Expressions 1 and 2]

$$(\text{First State Quantity}) = \frac{1}{N-1} \sum_{i=1}^{N-1} |X_{i+1} - X_i| \quad (1)$$

$$(\text{Second State Quantity}) = \sqrt{\frac{1}{N-1} \sum_{i=1}^{N-1} (X_{i+1} - X_i)^2} \quad (2)$$

The frequency distribution of the absolute values (|Xi+1−Xi|) of the first-order differences of the dislocation is as illustrated in FIG. 9 and FIG. 10. FIG. 9 illustrates the state during proper operation, wherein the frequency of occurrence falls smoothly with increasing magnitude of the difference values. On the other hand, if stick-slip occurs, then a majority of the time will be a stationary state, and then slipping will occur occasionally. Because of this, the frequencies of the first-order difference values will have high frequencies clustered around zero, as illustrated in FIG. 10, (corresponding to the stationary state), with relatively large values at low frequencies (corresponding to the slipping state). In the state wherein this type of stick-slip occurs, the ratio of the first state quantity (the average value of the absolute values of the first-order difference values) to the second state quantity (the root mean square of the first-order difference values) will be larger than during proper operation, making it possible to detect the occurrence of stick-slip by monitoring the two state quantities.

In the technology disclosed in JP '624, the detection is performed through the relationship of two state quantities calculated, from the dislocation of a moving portion, by calculating the motion that is subject to stick-slip detection, divided into a stationary state and a slipping state. This makes the determination using only the dislocation of the moving portion. Because of this, if the movement (dislocation) of the moving portion is similar to that of the stick-slip state, then an incorrect evaluation will be that there is stick-slip, even if the stick-slip has not actually occurred. This shall be termed "false stick-slip detection."

For example, in the control of a valve stem position in a regulator valve using a positioner, if there is a large change in the valve stem dislocation control instruction value (a setting opening), then the behavior of the dislocation of the valve stem (the moving portion) at the time of the change of the control instruction value may be similar to that of the stick-slip state.

As illustrated in FIG. 11 (*a*), when control instruction values for dislocations wherein the time-series signals form a square wave by alternating two values over time, then the response of the valve stem dislocation for the regulator valve can, accordingly, be measured as the dislocation measurement values for the time-series signals as illustrated in FIG. 11 (*b*). The first-order difference values in this type of dislocation measurement value can be as illustrated in FIG. 11 (*c*). In this case, as illustrated in FIG. 11 (*c*), the majority of the first-order difference values can be clustered near to zero, where only the values immediately after the control instruction value has changed will be large.

This behavior is identical to the behavior of the stick-slip phenomenon wherein there is a stationary state the majority of the time, with occasional rapid movement in the slipping state. The result is that, in the technology of JP '624, there can be false detection of the occurrence of stick-slip when control is performed as illustrated in FIG. 11 (*a*). This false detection tends to occur when the operating speed of the valve is high, and is particularly problematic in small valves.

Given this, the present applicant has proposed, as a method for controlling false detection of stick-slip, the technology disclosed in Japanese Unexamined Patent Application Publication 2011-80787 ("JP '787"). In the technology disclosed in JP '787 not only is a stick-slip indicator calculated from the dislocations, but from the control instruction values as well, where the stick-slip indicator that is calculated from the dislocations is defined as a first stick-slip indicator and the stick-slip indicator that is calculated from the control instruction values is defined as a second stick-slip indicator, where if the second stick-slip indicator is greater than the first stick-slip indicator, then the stick-slip detection is not applicable.

That is, when a control instruction value is applied that causes an operation wherein it is concluded that a stick-slip has occurred, the dislocation of a movable portion that is operating properly behaves more smoothly than the control instruction value. In this case, the second stick-slip indicator, which is calculated from the control instruction values, is larger than the first stick-slip indicator, which is calculated from the dislocations of the sliding portion. Consequently, it is possible to prevent false detection of stick-slip by omitting from applicability of stick-slip detection those cases wherein the second stick-slip indicator is greater than the first stick-slip indicator.

However, the technology disclosed in JP '787 cannot be said to be perfect, and cannot be said to be able to prevent, with high accuracy, false detection of stick-slip.

FIGS. 12 (a) and (b) show a comparison of changes in control instruction values when it has been possible to control false detection of the stick-slip versus changes in control instruction values when it has not been possible. In both FIGS. 12 (a) and (b), actually the states are when stick-slip has not occurred, where FIG. 12 (a) is an example of having been able to control false detection of stick-slip and FIG. 12 (b) is an example wherein it has not been possible to control false detection of stick-slip.

In these examples, SSpv is the first stick-slip indicator, calculated from the dislocation, SSsp is the second stick-slip indicator, calculated from the control instruction values, and Th is a threshold value for evaluating proper operation/faulty for the first stick-slip indicator SSpv. Note that in this example, the threshold value Th is established as Th=10.

In both FIGS. 12 (a) and (b), the movement of the valve repeats between "stopped" and "rapid change in opening," such as in stick-slip, where, in FIG. 12 (a) the calculations are SSpv=16.00 and SSsp=16.97, and in FIG. 12 (b) the calculations are SSpv=10.32, and SSsp=10.26.

In FIG. 12 (a) SSpv is 16.00, and because this is greater than the threshold value Th=10 (SSpv>Th), then, by the technology disclosed in JP '624, this would be detected as an occurrence of stick-slip. However, SSsp is 16.97, which is equal to or greater than SSpv=16.00 (SSsp≥SSpv). Because of this, by the technology disclosed in JP '787, this is excluded from applicability of stick-slip detection. Consequently, false detection of stick-slip is prevented in the example illustrated in FIG. 12 (a).

In FIG. 12 (b) SSpv is 10.32, and because this is greater than the threshold value Th=10 (SSpv>Th), then, by the technology disclosed in JP '624, this would be detected as an occurrence of stick-slip. In this case, SSsp is 10.26, which is less than SSpv=10.32 (SSsp<SSpv). Because of this, by the technology disclosed in JP '787, this is not excluded from applicability of stick-slip detection. Consequently, false detection of stick-slip occurs in the example illustrated in FIG. 12 (b).

In this way, in the technology disclosed in JP '787 false detection of stick-slip will occur on occasion, and thus it cannot be said that false detection of stick-slip is prevented with high accuracy.

The present invention was created in order to solve such problems, and the object thereof is to provide a stick-slip detecting device and detecting method able to prevent, with high accuracy, false detection of stick-slip.

SUMMARY

In the examples of the present invention, in order to achieve the object set forth above, it includes a dislocation detecting means for detecting a dislocation of a movable portion having a contact sliding portion; first state quantity calculating means for calculating a first state quantity from the dislocation; second state quantity calculating means for calculating a second state quantity from the dislocation; first stick-slip indicator calculating means for calculating a ratio of the first state quantity and the second state quantity as a first stick-slip indicator based on dislocations; control instruction receiving means for receiving a control instruction value for controlling a dislocation of the movable portion; third state quantity calculating means for calculating a third state quantity from the control instruction value; fourth state quantity calculating means for calculating a fourth state quantity from the control instruction value; second stick-slip indicator calculating means for calculating a ratio of the third state quantity and the fourth state quantity as a second stick-slip indicator based on control instruction values; and fault evaluating means for concluding that there is a fault in the movable portion when the condition expression indicated by Expression (3), below, is satisfied when SSpv is the first stick-slip indicator, SSsp is the second stick-slip indicator, Th is a threshold value, α is a first constant, and β is a second constant:

$$SSpv > Th \text{ AND } SSpv > \alpha \cdot SSsp + \beta \qquad (3)$$

excluding the case of α=1, β=0 in Expression (3).

Given the present invention, only when Expression (3) is satisfied can it be detected as the occurrence of stick-slip. α and β in this Expression (3) may be adjusted to adjust the stick-slip detecting range. Doing so enables high accuracy tuning, based on actual results, of the stick-slip detecting range, making it possible to prevent false detection of stick-slip with high accuracy.

In the examples of the present invention, α and β are introduced as adjusting parameters. In this case, as one approach, for example, one may consider learning the relationship between the first and the second stick-slip indicators during proper operation, and setting the first constant α and the second constant β based on the relationship between the first and second stick-slip indicators when in a proper operating state, placing the first constant α and the second constant β, thus determined, into Expression (3), above.

As a different approach, one may consider learning the relationship between the first and the second stick-slip indicators when in a proper operating state and when in a faulty state, and based on the relationship that has been learned for the first and second stick-slip indicators in the proper operating state and in the faulty state, establishing the first constant α and the second constant β as decision criteria as to whether to emphasize prevention of false detection or to emphasize prevention of detection failure, and then setting into the first constant α and the second constant β that have been thus established, in Expression (3), above.

Note that examples of the present invention may be embodied also as a stick-slip preventing method, rather than a stick-slip preventing device.

Given the examples of the present invention, when SSpv is the first stick-slip indicator, SSsp is the second stick-slip indicator, Th is the threshold value, α is the first constant, and β is the second constant, then if the conditional expression indicated by Expression (3) is satisfied, the evaluation is that the movable portion is faulty, and thus it is possible to prevent, with high accuracy, false detection of stick-slip, by tuning, based on actual results, the stick-slip detecting range with high accuracy through the use of α and β as tuning parameters.

BRIEF DESCRIPTION OF THE DRAWINGS

FIG. 12 is a timing chart illustrating a comparison of the changes in the control instruction values when false detection of stick-slip is prevented, and the changes in the control instruction values when not prevented.

DETAILED DESCRIPTION

An example according to the present invention is explained below in detail, based on the drawings.

Figure 1:
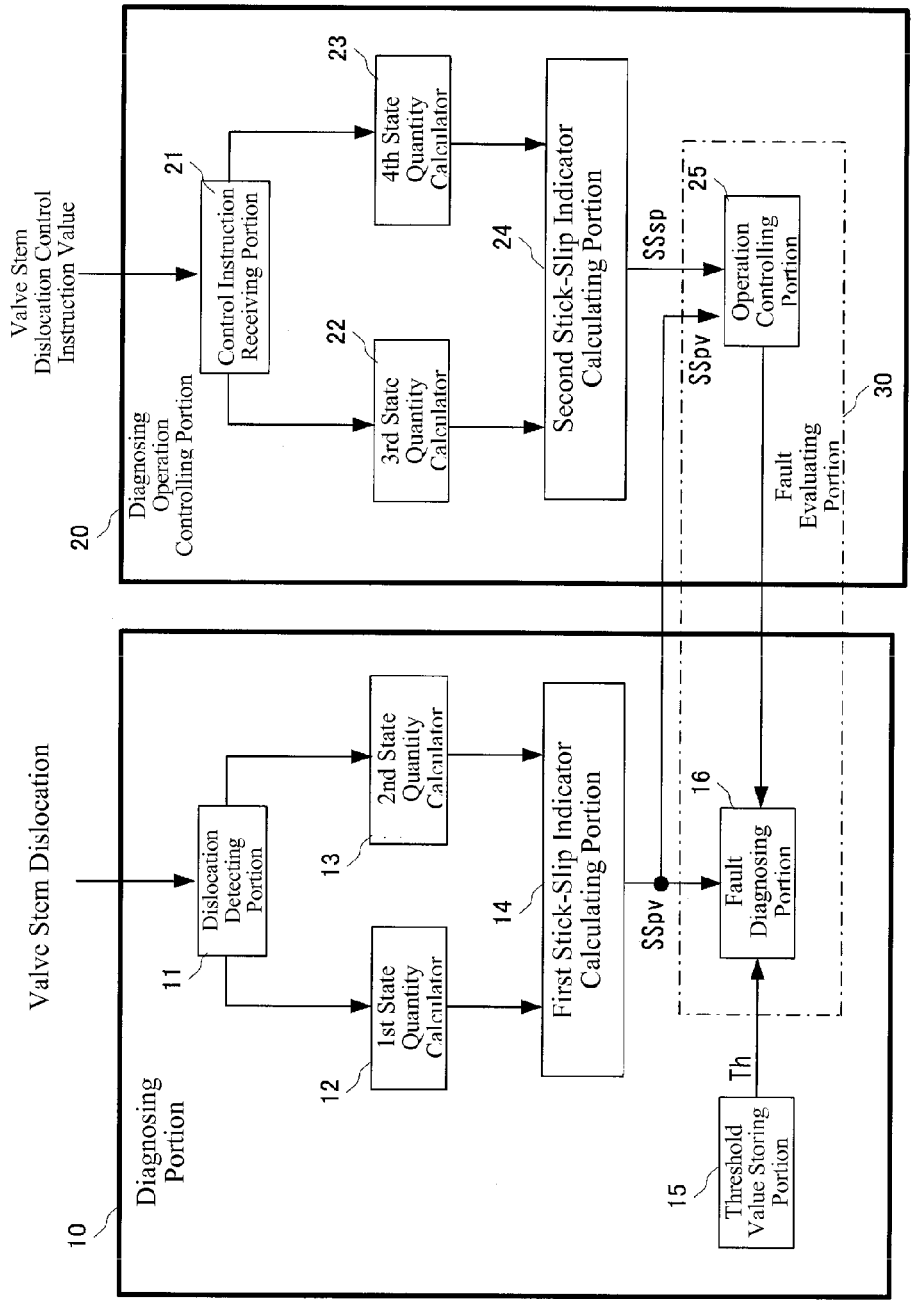
FIG. 1 is a diagram illustrating the critical portions of an example of a stick-slip detecting device according to the present invention.

FIG. 1 is a diagram illustrating portions of an example of a stick-slip detecting device according to the present invention. This stick-slip detecting device is provided with a diagnosing portion 10 for evaluating a fault based on the dislocation of a movable portion that has a contact sliding portion, and a diagnosing operation controlling portion 20 for stopping the operation of the diagnosing portion 10 based on a control instruction value for controlling the dislocation of the movable portion.

Note that in the present form of embodiment, the valve stem dislocation of a regulator valve that wherein the degree of opening is controlled by a positioner is used as the dislocation of the movable portion that has a contact sliding portion, and the control instruction value to the positioner for the valve stem dislocation is used as the control instruction value for controlling the dislocation of the movable portion.

The diagnosing portion 10 is provided with a dislocation detecting portion 11, a first state quantity calculator 12, a second state quantity calculator 13, a first stick-slip indicator calculating portion 14, a threshold value storing portion 15, and a fault diagnosing portion 16.

The dislocation detecting portion 11 detects a valve stem dislocation and outputs a dislocation signal that is, for example, a digital signal. The first state quantity calculator 12 calculates the average of the absolute values of the first-order difference values, as the first state quantity, from the dislocation signals from the dislocation detecting portion 11. The second state quantity calculator 13 calculates the root mean square of the first-order difference values, as the second state quantity, from the dislocation signals from the dislocation detecting portion 11.

The first stick-slip indicator calculating portion 14 calculates the ratio of the first state quantity, calculated by the first state quantity calculator 12, and the second state quantity, calculated by the second state quantity calculator 13, as the first stick-slip indicator SSpv that depends on dislocations.

The threshold value storing portion 15 stores a threshold value Th for evaluating the proper operation/fault of the first stick-slip indicator SSpv. The fault diagnosing portion 16 compares the first stick-slip indicator SSpv, calculated by the first stick-slip indicator calculating portion 14, to the threshold value Th, stored in the threshold value storing portion 15, and if SSpv>Th, concludes that a stick-slip has occurred.

On the other hand, the diagnosing operation controlling portion 20 is provided with a control instruction receiving portion 21, a third state quantity calculator 22, a fourth state quantity calculator 23, a second stick-slip indicator calculating portion 24, and an operation controlling portion 25.

The control instruction receiving portion 21 receives the control instruction value to the positioner for the valve stem dislocation. The third state quantity calculator 22 calculates the average of the absolute values of the first-order difference values, as the third state quantity, from the control instruction values received by the control instruction receiving portion 21. This is an identical operation to that of the first state quantity calculator 12 that calculates the average of the absolute values of the first-order difference values, as the first state quantity, from the dislocation signals that have been detected.

The fourth state quantity calculator 23 calculates the root mean square of the first-order difference values, as the fourth state quantity, from the control instruction values received by the control instruction receiving portion 21. This is an identical operation to that of the second state quantity calculator 13 that calculates the root mean square of the first-order difference values, as the second state quantity, from the dislocation signals that have been detected.

The second stick-slip indicator calculating portion 24 calculates a ratio of the third state quantity, calculated by the third state quantity calculator 22, and the fourth state quantity, calculated by the fourth state quantity calculator 23, as the second stick-slip indicator SSsp that depends on the control instruction value.

The operation controlling portion 25 inputs the first stick-slip indicator SSpv from the first stick-slip indicator calculating portion 14 in the diagnosing portion 10 and the second stick-slip indicator SSsp from the second stick-slip indicator calculating portion 24, and if SSpv≤α·SSsp+β, stops the evaluating operation of the fault diagnosing portion 16. Note that α is a first constant and β is a second constant, established through a learning process, described below.

In the present example, a fault evaluating portion 30 that corresponds to the fault evaluating means as stated in the present invention is structured from the fault diagnosing portion 16 in the diagnosing portion 10 and the operation controlling portion 25 in the diagnosing operation controlling portion 20. This fault evaluating portion 30 concludes, through a combination of the operations of the fault diagnosing portion 16 and the operation controlling portion 25, that a stick-slip has occurred when the conditional expression "SSpv>Th AND SSpv>α·SSsp+β" is satisfied.

Figure 2:
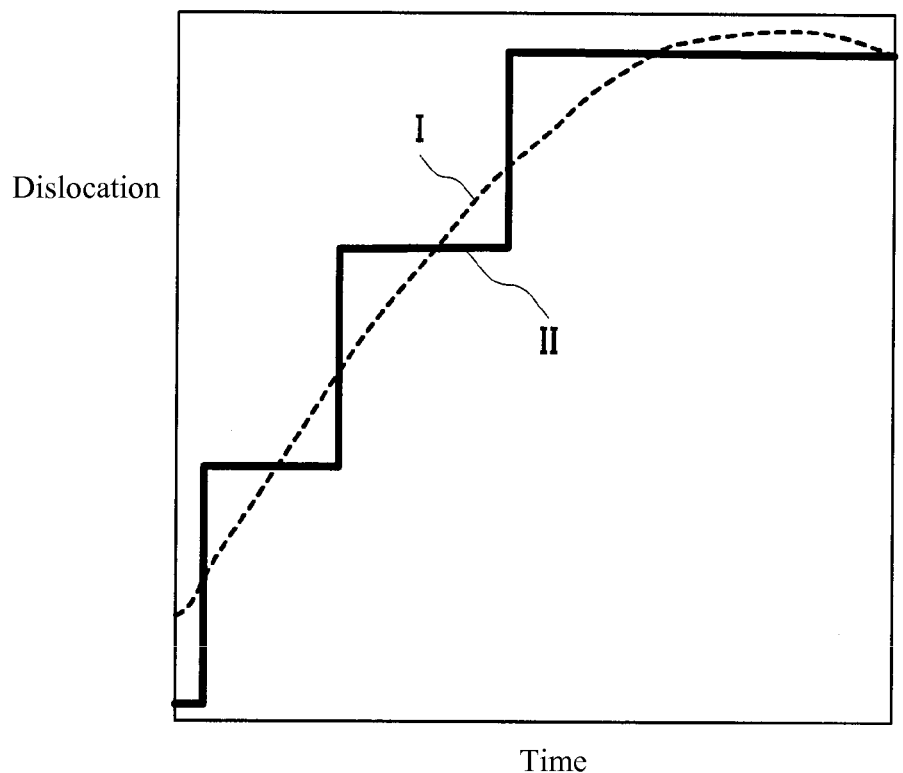
FIG. 2 is a diagram illustrating the relationship between the control instruction values and the dislocation signals obtained.

First let us consider the case wherein the control instruction values for the dislocation as illustrated by the dotted line in FIG. 2 are applied in the stick-slip detecting device. If the valve stem operates properly for these control instruction values, then the dislocation signal that is detected and outputted by the dislocation detecting portion 11 can also be in the same state, and the fault diagnosing portion 16 does not conclude that a stick-slip has occurred. Additionally, if the third state quantity and the fourth state quantity are calculated based on the control instruction values in this way, then the first stick-slip indicator SSpv that indicates the ratio of the first state quantity and the second state quantity can be larger than the second stick-slip indicator SSsp that indicates the ratio of the third state quantity and the fourth state quantity (SSpv>SSsp).

On the other hand, when a stick-slip has occurred, then the dislocation signal that is detected and outputted by the dislocation detecting portion 11 can have a stair-step shape as indicated by the solid line II in FIG. 2. When this type of dislocation signal is detected, then the fault diagnosing portion 16 concludes that a stick-slip has occurred. In this case as well, the first stick-slip indicator SSpv that indicates the ratio of the first state quantity and the second state quantity can be larger than the second stick-slip indicator SSsp that indicates the ratio of the third state quantity and the fourth state quantity (SSpv>SSsp).

Figure 3:
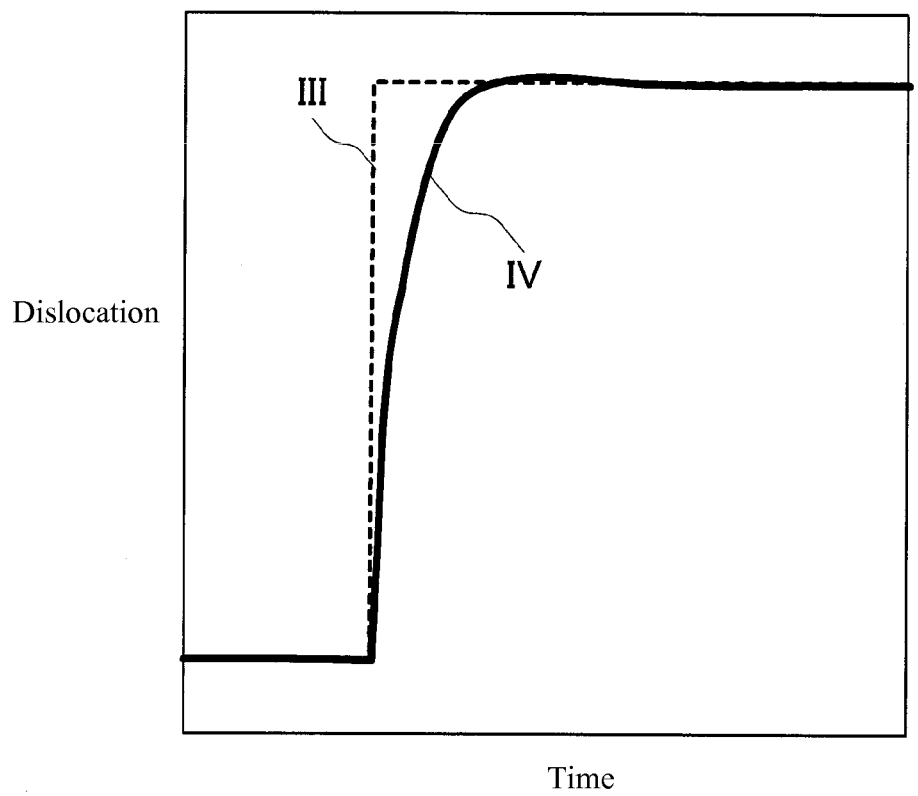
FIG. 3 is a diagram illustrating the relationship between the control instruction values and the dislocation signals obtained.

In contrast to the case set forth above, let us consider a case wherein a control instruction signal for a dislocation indicated by the dotted line III in FIG. 3 is applied. When control instruction values of this type are applied, then even if the valve stem is operating properly, the dislocation signal detected by the dislocation detecting portion 11 can appear as shown by the solid line IV in FIG. 3. In such a state, the fault diagnosing portion 16 can conclude that a stick-slip has occurred. Here, if the third state quantity and the fourth state quantity are calculated based on the control instruction values, then the second stick-slip indicator SSsp that indicates the ratio of the third state quantity and the fourth state quantity can be equal to or greater than the first stick-slip indicator SSpv that indicates the ratio of the first state quantity and the second state quantity (SSsp≥SSpv).

Consequently, stopping the evaluating operation of the fault evaluating portion 16 when it is detected that the second stick-slip indicator SSsp, which depends on control instruction values, is equal to or greater than the first stick-slip indicator SSpv, which depends on dislocations (SSsp≥SSpv), or in other words, enabling the evaluating operation of the fault evaluating portion 16 only when SSpv>SSsp, makes it possible to prevent a false detection of stick-slip.

However, merely having SSpv>SSsp is the same as the technology disclosed in Patent Document 2, which is unable to prevent false detection of stick-slip with high accuracy. Given this, the adjusting parameters α and β have been introduced in the present form of embodiment, making it possible to enable the evaluating operation of the fault diagnosing portion 16 in the fault evaluating portion 30 only when SSpv>α·SSsp+β. This is achieved through the operation controlling portion 25 stopping the operation the evaluating operation of the fault diagnosing portion 16 in the diagnosing portion 10 when SSpv≤α·SSsp+β.

In this case, if the conditional expression indicated by Expression (4), below, is satisfied, the fault evaluating portion 30 concludes that a stick-slip has occurred. Note that if, in this conditional expression, α=1 and β=0, then this will be identical to JP '787. Because of this, in the present examples of the invention, the case of α=1 and β=0 is excluded:

$$SSpv > Th \text{ AND } SSpv > \alpha \cdot SSsp + \beta \quad (4)$$

A Learning Process for Adjusting α and β Through Learning

In order to calculate α and β, which are the adjusting parameters, the following learning process can be performed during the inspection test operations at the time of factory shipment or during process control.

(1) Stick-slip indicators SSpv that are based on dislocations and stick-slip indicators SSsp that are based on control instruction values are calculated when in a proper operating condition wherein stick-slip does not occur.

Figure 4:
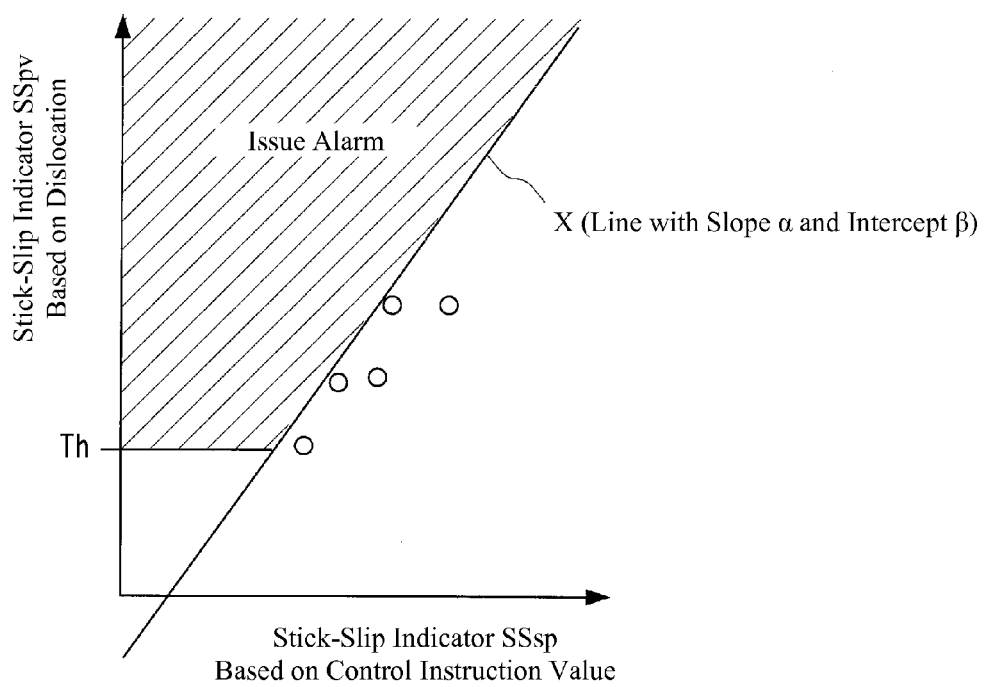
FIG. 4 is a diagram illustrating an example of calculating the slope α and the intercept β of a line X that serves as a boundary line for issuing an alarm when plotting stick-slip indicators when in a proper operating state.

(2) The stick-slip indicators SSpv that are based on dislocation and the stick-slip indicators SSsp that are based on the control instruction values, calculated in (1) are plotted on the stick-slip indicator plane illustrated in FIG. 4. In FIG. 4, the circle marks are plot points for the stick-slip indicators.

(3) A slope α and intercept β of a line X that is a boundary line for issuing an alarm are determined so that there will be no false detection of the states that have been plotted in (2).

(4) The α and β that have been determined in this way are placed into Expression (4), above.

Here several variations may be considered for the method for establishing the slope α and the intercept β of the line X. For example, β may be held constant at 0 and α alone may be increased until false detection rate goes to zero, or, conversely, α may be held constant and β may be increased until false detection rate goes to zero.

Figure 5:
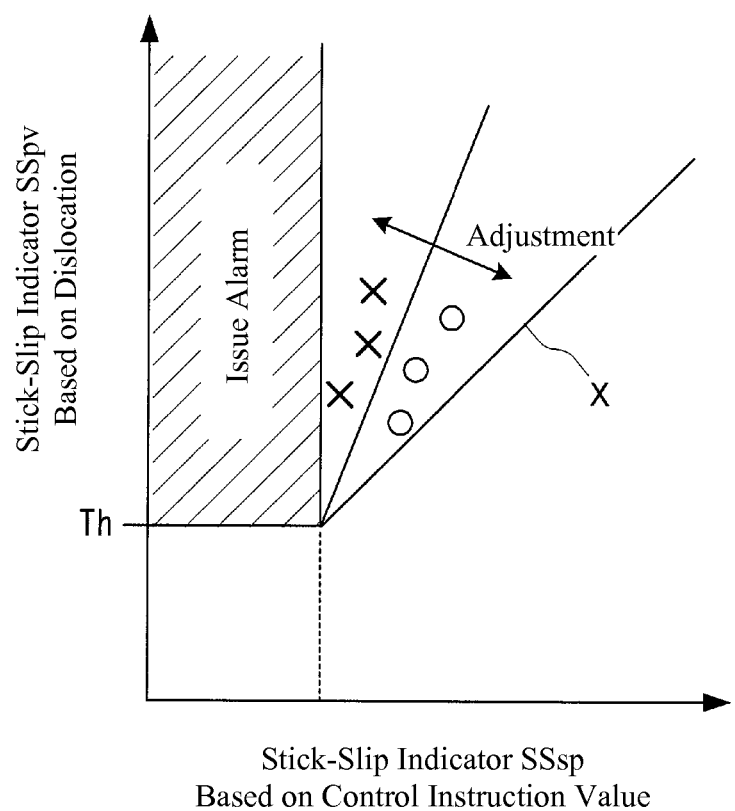
FIG. 5 is a diagram illustrating an example of calculating the slope α and the intercept β of a line X that serves as a boundary line for issuing an alarm when plotting stick-slip indicators when in a proper operating state and stick-slip indicators when in a faulty state.

Note that if data wherein a stick-slip has actually occurred can be obtained, then it becomes possible to also learn so as to simultaneously increase the detection rate (the correct detection rate) while keeping the false detection rate as low as possible. For example, α and β may be determined through linear discriminant analysis, or the like. Moreover, a non-linear discriminant technique, such as in a support vector machine, may be applied instead. FIG. 5 shows a schematic diagram thereof.

In FIG. 5, the slope of the line X is varied using, as a fulcrum, the point wherein both the stick-slip indicators SSsp that are based on the control instruction value and the stick-slip indicators SSpv that are based on the dislocation go to the threshold value Th, to adjust the stick-slip detecting range (the region for issuing an alarm). Note that in FIG. 5 the circle marks indicate the plot points for stick-slip indicators in a proper operating state, and the X marks are plot points for stick-slip indicators in a faulty state.

Figure 6:
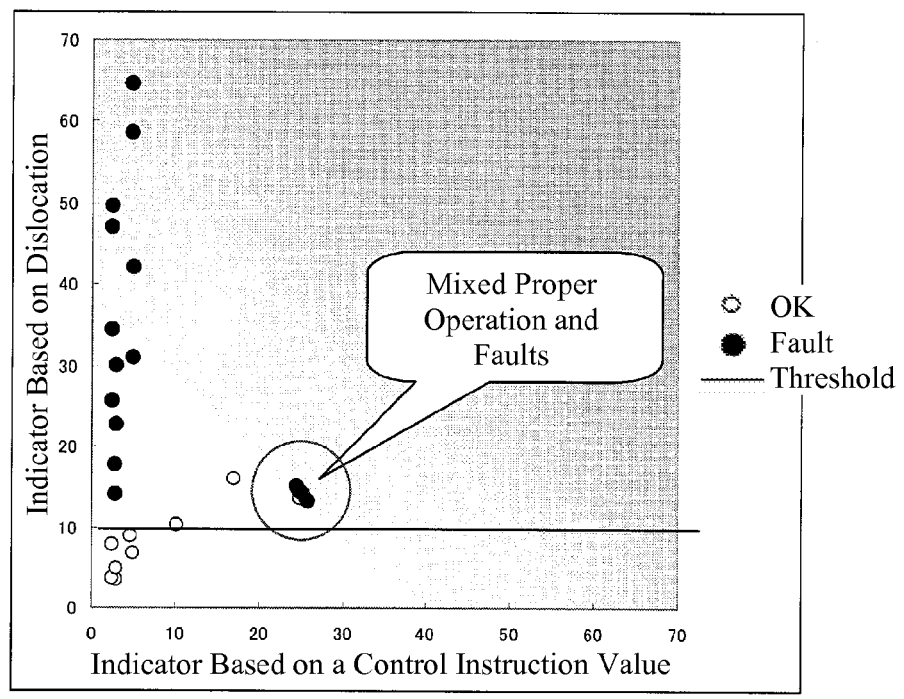
FIG. 6 is a diagram illustrating an example of plotting the results of calculating stick-slip indicators under a variety of conditions relative to a control valve of a given model.

FIG. 6 is a plot of the result of calculating stick-slip indicators under a variety of conditions for a control valve of a particular model. The "fault (dark circle marks)" are data for the case wherein forces wherein stick-slip occurs are applied to the valve stem. The "proper operation (white circle marks)" are when stick-slip did not occur, without applying the force to the valve stem.

Figure 7:
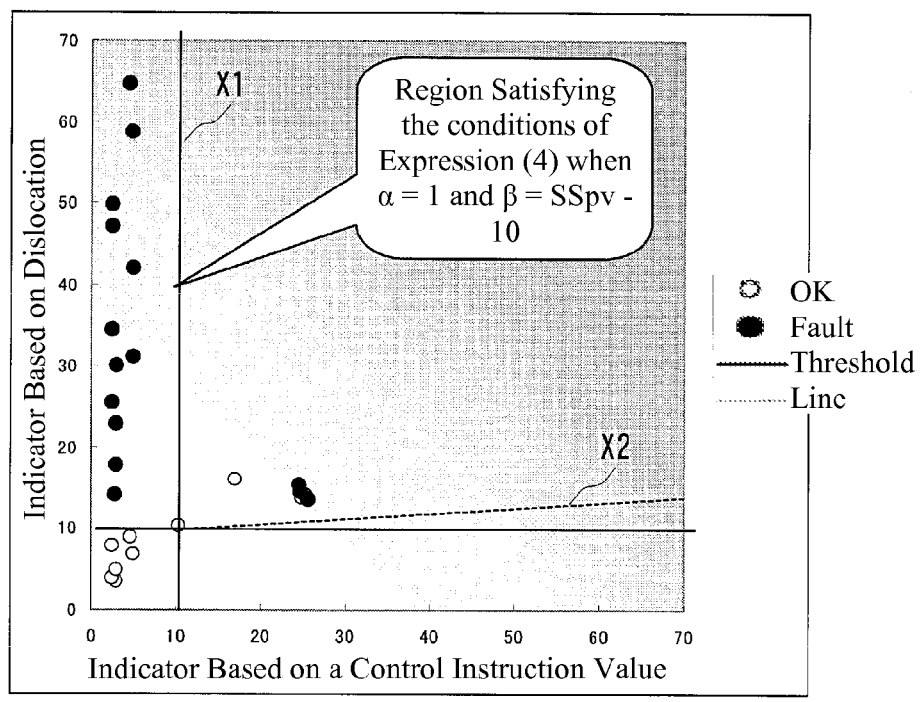
FIG. 7 is a diagram illustrating an example of a line X1 that serves as a boundary line for issuing an alarm when emphasizing prevention of false detection and an example of a line X2 that serves as a boundary line for issuing an alarm when emphasizing prevention of detection failures.
Figure 8:
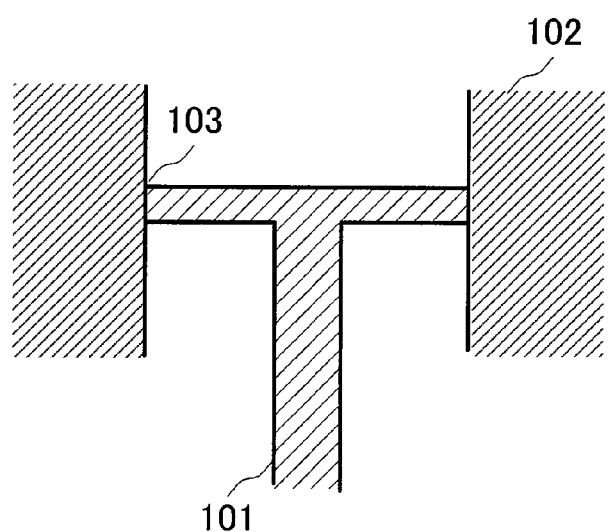
FIG. 8 is a diagram illustrating the structure of a device having a contact sliding part.
Figure 9:
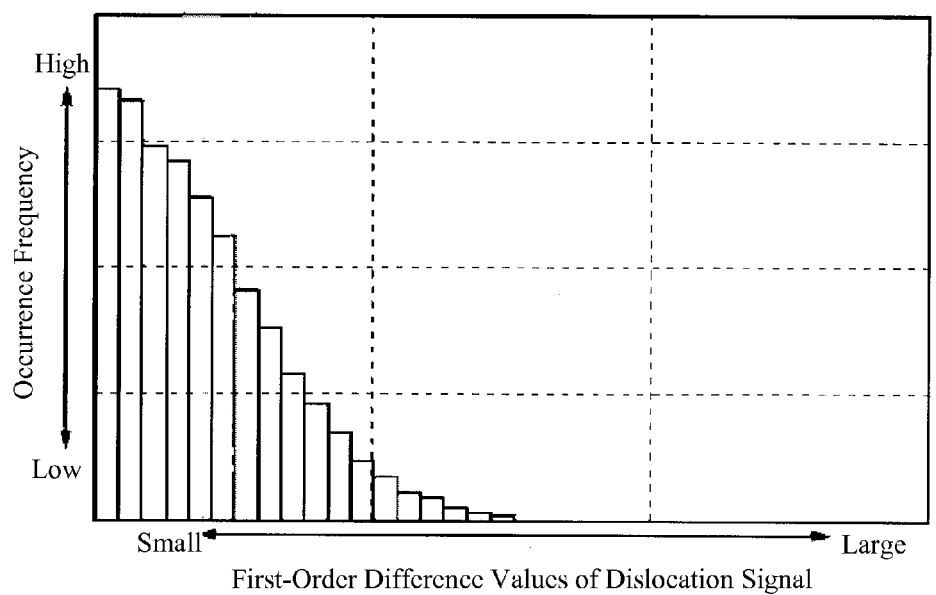
FIG. 9 is a histogram illustrating the distribution of the frequency of occurrences of first-order difference values in a dislocation signal obtained from a part that undergoes reciprocating sliding (for the case wherein stick-slip does not occur).
Figure 10:
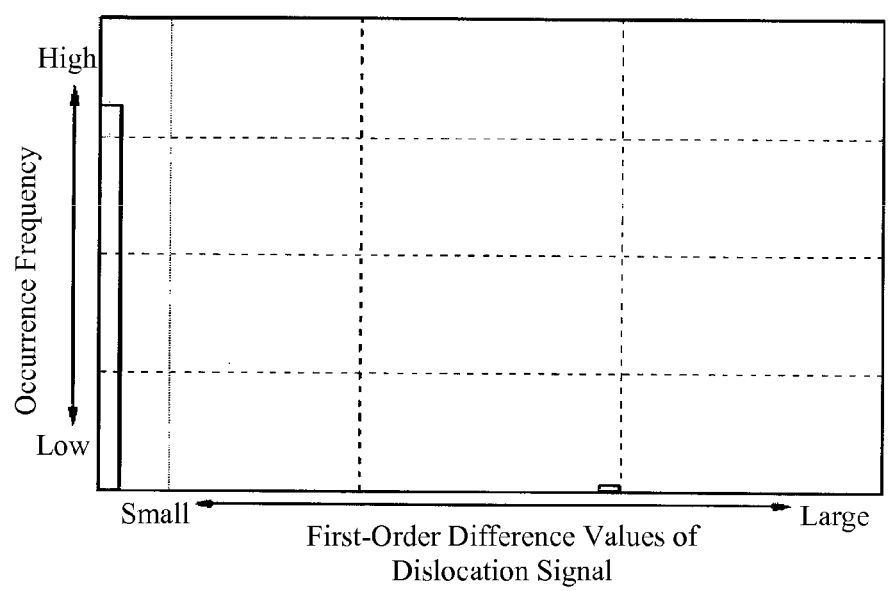
FIG. 10 is a histogram illustrating the distribution of the frequency of occurrences of first-order difference values in a dislocation signal obtained from a part that undergoes reciprocating sliding (for the case wherein stick-slip does occur).
Figure 11:
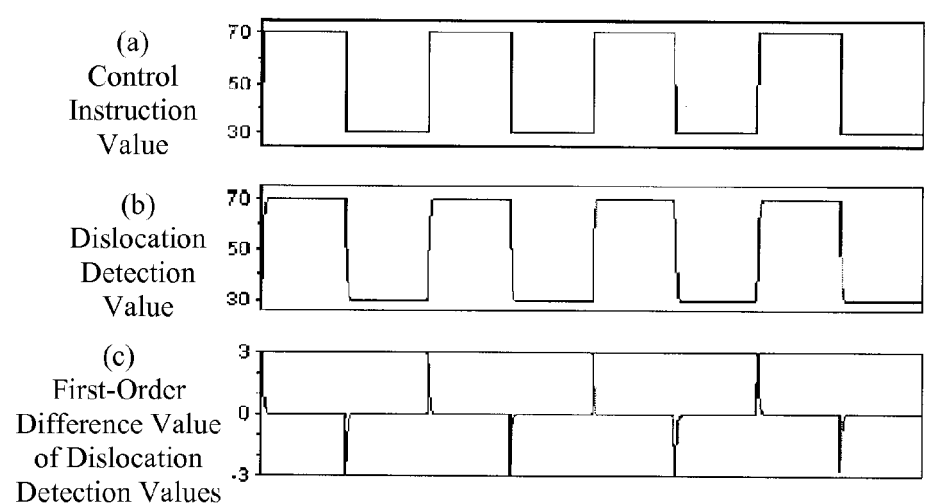
FIG. 11 is a timing chart illustrating the changes in the control instruction values, the dislocation measurement values, and the first-order difference values of the dislocation detection values.

In the example in FIG. 6, when the control instruction values are large, then there is a mixture of proper operation and faults. If here the emphasis is on preventing false detection, then, as illustrated by the line X1, which is the solid line in FIG. 7, α should be set to 1 and β should be set to SSpv−10 in the "SSpv>α·SSsp+β in Expression (4), above. That is, "SSpv>α·SSsp+β" should be "10>SSsp". Note that in this case there can still be the risk of detection failure. Moreover, if the emphasis is on preventing detection failure, then, as indicated by the line X2, which is the dotted line in FIG. 7, the slope α should be set small, to approach a straight line at the threshold value Th. Note that in this case there can be the risk of falsely detecting proper operation as a fault.

Note that while in the example set forth above averages of the absolute values of the first-order difference values were calculated as the first state quantity and the third state quantity and root mean squares of first-order difference values were calculated as the second state quantity and the fourth state quantity, there is no limitation thereto. For example, instead root mean squares of first-order difference values may be calculated as the first state quantity and the third state quantity, and averages of the absolute values of first-order difference values may be calculated as the second state quantity and the fourth state quantity.

Moreover that the stick-slip detection set forth above may detect the stick-slip through processing the detected dislocations using a computer. For example, a CPU that structures a computer may be operated through a program that is deployed in a memory that is connected through a bus, to process the dislocation signal that is obtained to output diagnosis results, and the processing that produces the diagnosis results may be stopped by the obtained control instruction values.

Here the aforementioned program may run, on a CPU (a computer), the process for the stick-slip detection explained in any of the forms of embodiment described above. Furthermore, the program that is deployed in memory may be stored on an external memory device that is connected externally through a bus and then deployed. The external storage device may be, for example, a magnetic disk storage device.

While the present invention has been explained above in reference to examples, the present invention is not limited to the examples set forth above. The structures and details in the present invention may be varied in a variety of ways, as can be understood by one skilled in the art, within the scope of technology in the present invention.

I claim:

1. A stick-slip detecting device for a movable portion of a valve or gas governor, comprising:
   a dislocation detector detecting a physical dislocation of the movable portion having a contact sliding portion;
   a first state quantity calculator calculating a first state quantity from the physical dislocation;
   a second state quantity calculator calculating a second state quantity from the physical dislocation;
   a first stick-slip indicator calculator calculating a ratio of the first state quantity and the second state quantity as a first stick-slip indicator based on the physical dislocations;
   a control instruction receiver receiving a control instruction value controlling a physical dislocation of the movable portion;
   a third state quantity calculator calculating a third state quantity from the control instruction value;
   a fourth state quantity calculator calculating a fourth state quantity from the control instruction value;
   a second stick-slip indicator calculator calculating a ratio of the third state quantity and the fourth state quantity as a second stick-slip indicator based on control instruction values; and
   a fault evaluator concluding that there is a fault in the movable portion when the condition expression indicated by Expression (1), below, is satisfied when SSpv is the first stick-slip indicator, SSsp is the second stick-slip indicator, Th is a threshold value, $\alpha$ is a first constant, and $\beta$ is a second constant:

$$SSpv > Th \text{ AND } SSpv > \alpha \cdot SSsp + \beta \quad (1)$$

excluding the case of $\alpha=1$, $\beta=0$ in Expression (1)

wherein the movable portion is a piston;
   wherein the contact sliding portion is an interior surface of a chamber that houses the piston;
   wherein the first and the third state quantities are calculated by Expression (2):

$$\frac{1}{N-1} \sum_{i=1}^{N-1} |X_{i+1} - X_i|$$

wherein the second and the fourth state quantities are calculated by Expression (3):

$$\sqrt{\frac{1}{N-1} \sum_{i=1}^{N-1} (X_{i+1} - X_i)^2}$$

and
   wherein for the first and second state quantities N is the number of physical dislocations, and
   wherein for the third and fourth state quantities N is the number of control instruction values.

2. The stick-slip detecting device for a movable portion of a valve or gas governor, as set forth in claim 1, comprising:
   a stick-slip indicator learning device learning a relationship of the first and second stick-slip indicators in a proper operating state; and
   a constant setting device setting, into the Expression (1), a first constant $\alpha$ and a second constant $\beta$ that are established based on the learned relationship for the first and second stick-slip indicators in the proper operating state.

3. The stick-slip detecting device for a movable portion of a valve or gas governor, as set forth in claim 1, comprising:
   a stick-slip indicator learning device learning a relationship of the first and second stick-slip indicators in a proper operating state and in a faulty state; and
   a constant setting device setting, into the Expression (1), the first constant $\alpha$ and the second constant $\beta$ determined based on the learned relationships of the first and second stick-slip indicators when in a proper operating state and when in a fault state, as decision criteria emphasizing prevention of false detection or emphasizing prevention of detection failure.

4. A stick-slip detecting method for a movable portion of a valve or gas governor, comprising the steps of:
   detecting a physical dislocation of the movable portion having a contact sliding portion;
   calculating a first state quantity depending on the physical dislocation;
   calculating a second state quantity depending on the physical dislocation;
   calculating a ratio of the first state quantity and the second state quantity as a first stick-slip indicator based on the physical dislocations;
   receiving a control instruction value controlling a physical dislocation of the movable portion;
   calculating a third state quantity depending on the control instruction value;
   calculating a fourth state quantity depending on the control instruction value;
   calculating a ratio of the third state quantity and the fourth state quantity as a second stick-slip indicator based on control instruction values;
   concluding that there is a fault in the movable portion when the condition expression indicated by Expression (2), below, is satisfied when SSpv is the first stick-slip indicator, SSsp is the second stick-slip indicator, Th is a threshold value, α is a first constant, and β is a second constant:

$$SSpv > Th \text{ AND } SSpv > \alpha \cdot SSsp + \beta \quad (2)$$

excluding the case of α=1, β=0 in Expression (2)
wherein the movable portion is a piston;
wherein the contact sliding portion is an interior surface of a chamber that houses the piston;
wherein the first and the third state quantities are calculated by Expression (2):

$$\frac{1}{N-1} \sum_{i=1}^{N-1} |X_{i+1} - X_i|$$

wherein the second and the fourth state quantities are calculated by Expression (3):

$$\sqrt{\frac{1}{N-1} \sum_{i=1}^{N-1} (X_{i+1} - X_i)^2}$$

wherein for the first and the second state quantities N is the number of physical dislocations, and
wherein for the third and the fourth state quantities N is the number of control instruction values.

5. The stick-slip detecting method for a movable portion of a valve or gas governor, as set forth in claim 4, comprising the steps of:
  learning a relationship of the first and second stick-slip indicators in a proper operating state; and
  setting, into the Expression (2), a first constant α and a second constant β that are established based on the learned relationship for the first and second stick-slip indicators in the proper operating state.

6. The stick-slip detecting method for a movable portion of a valve or gas governor, as set forth in claim 4, comprising:
  learning a relationship of the first and second stick-slip indicators in a proper operating state and in a faulty state; and
  setting, into the Expression (2), the first constant α and the second constant β determined based on the learned relationships of the first and second stick-slip indicators when in a proper operating state and when in a fault state, as decision criteria emphasizing prevention of false detection or emphasizing prevention of detection failure.

\* \* \* \* \*